(12) United States Patent  
Wilson

(10) Patent No.: US 7,184,515 B2
(45) Date of Patent: Feb. 27, 2007

(54) COMPONENT SPECIFIC MACHINE WEAR DETERMINATION WITH X-RAY FLUORESCENCE SPECTROMETRY

(75) Inventor: Bary Wilson, Coconut Creek, FL (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/949,962

(22) Filed: Sep. 24, 2004

(65) Prior Publication Data

US 2006/0067465 A1 Mar. 30, 2006

(51) Int. Cl.
G01N 23/223 (2006.01)
(52) U.S. Cl. .......................... 378/47; 378/44
(58) Field of Classification Search ............ 378/44–50; 73/49.7, 119 R
See application file for complete search history.

(56) References Cited

U.S. PATENT DOCUMENTS

| | | | |
|---|---|---|---|
| 2,315,845 A | 4/1943 | Ferris et al. | |
| 2,939,011 A | 5/1960 | Bisso et al. | |
| 3,751,661 A | 8/1973 | Packer et al. | |
| 3,936,192 A | 2/1976 | Skala | |
| 4,013,953 A | 3/1977 | Skala | |
| 4,125,769 A | 11/1978 | Marten et al. | |
| 4,388,530 A | 6/1983 | Lubecki et al. | |
| 4,450,576 A | 5/1984 | Lubecki et al. | |
| 4,620,185 A * | 10/1986 | Plahmer | 340/682 |
| 4,683,759 A | 8/1987 | Skarsvaag et al. | |
| 4,720,842 A | 1/1988 | Kira et al. | |
| 4,795,903 A | 1/1989 | Clayton | |
| 4,821,301 A | 4/1989 | Cocks et al. | |
| 5,000,036 A | 3/1991 | Yellowley et al. | |
| 5,187,542 A | 2/1993 | Madzsar | |
| 5,194,410 A | 3/1993 | Calabro | |
| 5,194,910 A | 3/1993 | Kirkpatrick, Jr. et al. | |
| 5,497,008 A | 3/1996 | Kumakhov | |
| 5,598,451 A | 1/1997 | Ohno et al. | |
| 5,657,363 A | 8/1997 | Hossain et al. | |
| 5,712,891 A | 1/1998 | Benony et al. | |
| 5,982,847 A * | 11/1999 | Nelson | 378/47 |
| 5,993,298 A | 11/1999 | Duescher | |
| 6,012,325 A | 1/2000 | Ma | |
| 6,080,982 A | 6/2000 | Cohen | |
| 6,226,347 B1 | 5/2001 | Golenhofen | |
| 6,285,734 B1 | 9/2001 | von Alfthan | |
| 6,306,319 B1 | 10/2001 | Swain et al. | |
| 6,408,048 B2 | 6/2002 | Opsal et al. | |
| 6,510,726 B1 | 1/2003 | Subramanyan et al. | |
| 2002/0083761 A1 | 7/2002 | Swain et al. | |
| 2003/0128805 A1* | 7/2003 | Shepard et al. | 378/47 |

* cited by examiner

*Primary Examiner*—Edward J. Glick
*Assistant Examiner*—Hoon Song
(74) *Attorney, Agent, or Firm*—Douglas E. McKinley, Jr.; John M. Bradshaw

(57) ABSTRACT

X-ray fluorescence analysis is used to determine wear of machine parts on a component-specific basis. The individual wetted wear surfaces of the machine are provided with a signature tagant composition, and as the components wear, the amounts of each tagant in the lubricating fluid are determined by the x-ray fluorescence analysis. An analysis system tracks the amounts of the tagants in the lubricating fluid, and with information of the signature tagant composition of each wear surface, calculates wear rate information for each of the wear surfaces. This component-specific wear information is then used in scheduling maintenance and predicting failures of the machine.

7 Claims, 3 Drawing Sheets

COMPONENT SPECIFIC MACHINE WEAR DETERMINATION WITH X-RAY FLUORESCENCE SPECTROMETRY

BACKGROUND

The present invention relates generally to machine wear detection, and more particularly, but not exclusively, to component-specific wear determination by analysis of a lubricating fluid.

Machines perform a variety of valuable functions in industry, but they require ongoing maintenance. Because of the costs associated with performing both preventative and corrective maintenance, significant attention is given to developing and implementing efficient maintenance programs. The general goal of most maintenance programs is to protect the machine and prolong its useful life while minimizing down time and other maintenance expenses.

Some maintenance programs are schedule-based. In these, intervals are established for certain preventative maintenance tasks, such as inspection or replacement of certain components or groups of components, and the task is performed upon the expiration of the interval. However, too frequent preventative maintenance is costly, in terms of labor, materials and the loss of use during the needed machine down time. Conversely, increasing the preventative maintenance intervals increases the chance a machine will fail during use, which itself can be costly as well as dangerous and inconvenient. Furthermore, some failures, such as where a component malfunctions due to damage, an inherent defect, improper installation, etc. are often unpredictable and therefore are difficult to head off with preventative maintenance performed solely on a calendar based or use based schedule. Condition-based maintenance programs are attempts to efficiently address these concerns and to reduce the risks of machine failures by determining maintenance, at least in part, based on measurements of the actual condition of the machine.

In a condition-based maintenance program, data is gathered in an effort to ascertain the physical condition of the machine and its various components. This data is then used to guide the scheduling of maintenance, for example by establishing safe limits for a certain measured parameter and then determining the need for maintenance when the measured value exceeds those limits. Since the condition of the machine's fluids can provide information about the condition of the machine, measurements performed on the machine's fluids are a useful source of input data for condition-based maintenance programs. For example, when the moving parts of a machine experience wear, fine particles are typically dispersed into the machine's lubricating fluid. A determination of the amount of these fine particles in the fluid therefore can be used to assess the amount of the machine wear.

However, the simple quantification of fine particles in the lubricating fluid is a non-specific indication of wear. In other words, the fine particles may have originated from various sources, each of which can be experiencing wear. As a result, particle count measurements can fail to capture the true state of the machine, and this potential for error increases as the number of wearing parts increases. For example, a gas turbine engine may have several bearings along a drive shaft. Accordingly, a situation could arise where one of these bearing wears at an abnormally high rate, putting the engine at risk of failure. However, the remaining bearings could wear at sufficiently low rates that the overall quantity of wear material in the lubricating fluid of the bearings does not indicate any impending failure. Unfortunately, the ability to detect such a condition or to otherwise provide component-specific wear information in machines is limited. Accordingly, there is a need for systems and techniques that obtain more specific machine wear information, and in certain forms, the present invention addresses this need. In these or in other forms the present invention provides useful and cost effective improvements for the condition-based maintenance of machines.

SUMMARY OF THE INVENTION

The present invention provides systems and techniques for component specific wear determinations through the x-ray fluorescence analysis of machine fluids. While the actual nature of the invention covered herein can only be determined with reference to the claims appended hereto, certain aspects of the invention that are characteristic of the embodiments disclosed herein are described briefly as follows.

In one embodiment, the present invention provides a method for monitoring wear of the wear surfaces of machine parts. The wear surfaces are provided with tagants, and x-ray fluorescence analysis of the lubricating fluid is employed to determine amounts of the tagants in the lubricating fluid. Each of the wear surfaces of the machine contains one or more of the tagants and the tagant composition of each wear surface is different. Thus, from the results of the x-ray fluorescence analysis, wear can be determined on a component specific basis.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying figures forming a part thereof.

DETAILED DESCRIPTION OF THE ILLUSTRATED EMBODIMENTS

Figure 1:
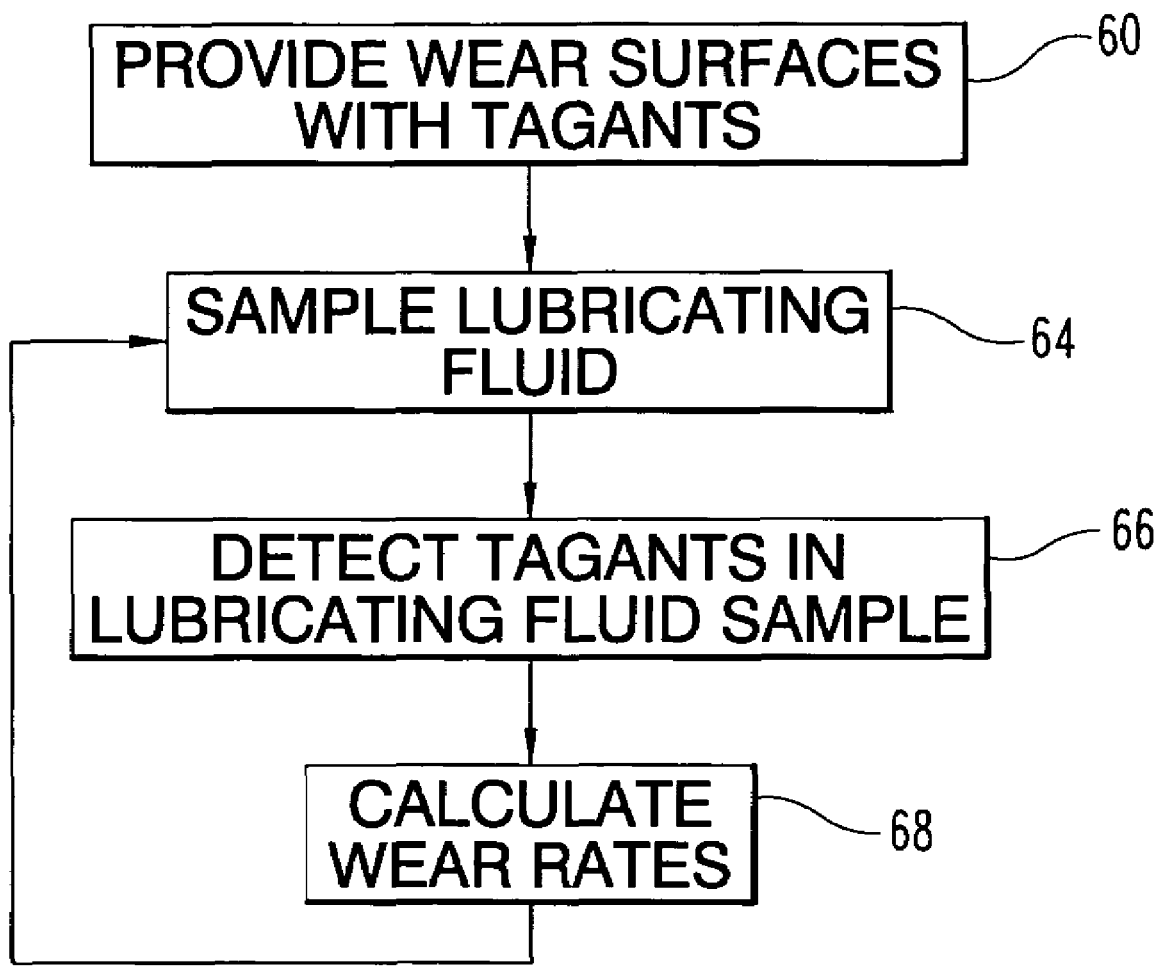
FIG. 1 flow diagram of a method for detecting wear of machine components.

For the purposes of promoting an understanding of the principles of the invention, reference will now be made to the embodiments illustrated in the drawings and specific language will be used to describe the same, where like reference numerals are used to describe like structures. Nevertheless, as it is the claims that define the invention, it is to be understood that no limitation of the scope of the invention is intended by any specific language used to describe the illustrated embodiments. Alterations and further modifications in the illustrated embodiments and further applications of the principles of the invention are contemplated as would normally occur to one skilled in the art to which the invention relates.

Briefly, in one aspect the present invention provides for the determination of machine component wear through the detection of tagants in a lubricating fluid. Tagants are material that has been provided in signature amounts in each of the wear surfaces of the various components. The tagants are not intended to influence the component's function, but rather are chosen to be detectable as the respective component wears via elemental analysis of the lubricating fluid. Because the signature tagant composition of each wear surface is different, the amounts of the tagants detected in the lubricating fluid can be associated with the individual wear surfaces to provide component specific wear information. This component-specific wear information may then be tracked and utilized in scheduling maintenance and predicting and preventing failures of the machine.

It is to be understood that tagants are elements or compounds that are incorporated into a wear surface for purposes of identification. A variety of materials could be employed, but substances that would cause significant deterioration in the mechanical wear properties of the wear surface are not good candidates for the tagants. Rather, in a typical application, these tagants will be materials that, while not ordinarily present in the wear surface, are compatible with the wear surfaces and do not lead to significant degradation of the performance of the wear surfaces, at least when incorporated in small amounts, e.g. around 1 atomic %. For example, where the wear surface is metallic, the tagants should be metallurgically compatible with the wear surface. An example would be metal atoms that fit into the metal matrix of the wear surface.

In a preferred embodiment, the tagants are selected such that, as the tagants are released into the lubricating as an incident to machine component wear, the tagants are detectable in the lubricating fluid via x-ray fluorescence analysis (XRF). It is to be appreciated that the use of x-ray fluorescence analysis allows the accurate determination of wear and wear rates even with only trace levels of the tagants in the lubricating fluid. As a result, the concentration of the tagants initially in the wear surfaces need not be very large, and in most cases will be very small. While the precise concentration of tagants in the wear surfaces will depend on the nature of the wear surface and the particular application, it is expected that useful tagant concentrations in the wear surface may be less than about 5 atomic %, for example between about 1 and 5 atomic %. Elements suitable for detection via XRF include those having an atomic number above 20 (calcium) and/or any of the metals in row 5 or higher of the periodic table. While any suitable compound or element may be employed in a given application, particularly suitable elements for use as tagants according to the present invention include vanadium, chromium, cobalt, gold, silver, tungsten and indium.

Referring to FIG. 1, a method for detecting wear of a machine on a component specific basis is depicted. The method involves providing the components with wear surfaces bearing tagants 60. The tagants may be uniformly distributed throughout the wear surfaces. Where a wear surface is composed of multiple layers, the tagants may be uniformly distributed in one or more of the layers of the wear surface. For example, the tagants can be dispersed in a laminated layer of a machine part. Alternatively, or in addition to uniform distribution throughout the wear surface, tagants can be confined to a discrete localized area or depth within the wear surface. This can be in the form of a pill or plug positioned beneath the initial wear surface or by confining the tagants to a layer (such as a laminated layer) beneath the surface that would be exposed after a certain amount of wear. Thus, the tagants are positioned at a predetermined wear depth and provide a means to determine when a particular level of wear has occurred.

It is to be understood that any of a variety of conventional mechanisms of material construction can be employed to incorporate, or dope, the tagants into the wear surfaces. For example, to achieve uniform distribution, the tagants can be added to the wear surfaces during initial construction of the wear surface by appropriate metallurgic alteration of the surface material. Tagants may also be doped into the surface, or a layer of the surface, via a deposition process, such as chemical vapor deposition (CVD). To achieve a discrete localized concentration of the tagants, a pill or plug containing the tagants can be machined into the wear surface.

Suitable parts constructed with the tagant-bearing wear surfaces can be a family of similar wear parts of an engine, for example a series of bearings or a series of pistons in an engine. This family of components, e.g. each of the bearings, will typically be of substantially identical material compositions save the difference in their composition of tagants. These parts are then incorporated into the machine to be monitored, and as the machine is used the lubricating fluid, which is in fluid communication with each of the parts, is sampled 64. The sampling is preferably continuous or substantially continuous, such as with an in-line sensor, but intermittent or batch sampling can also be employed.

Figure 3:
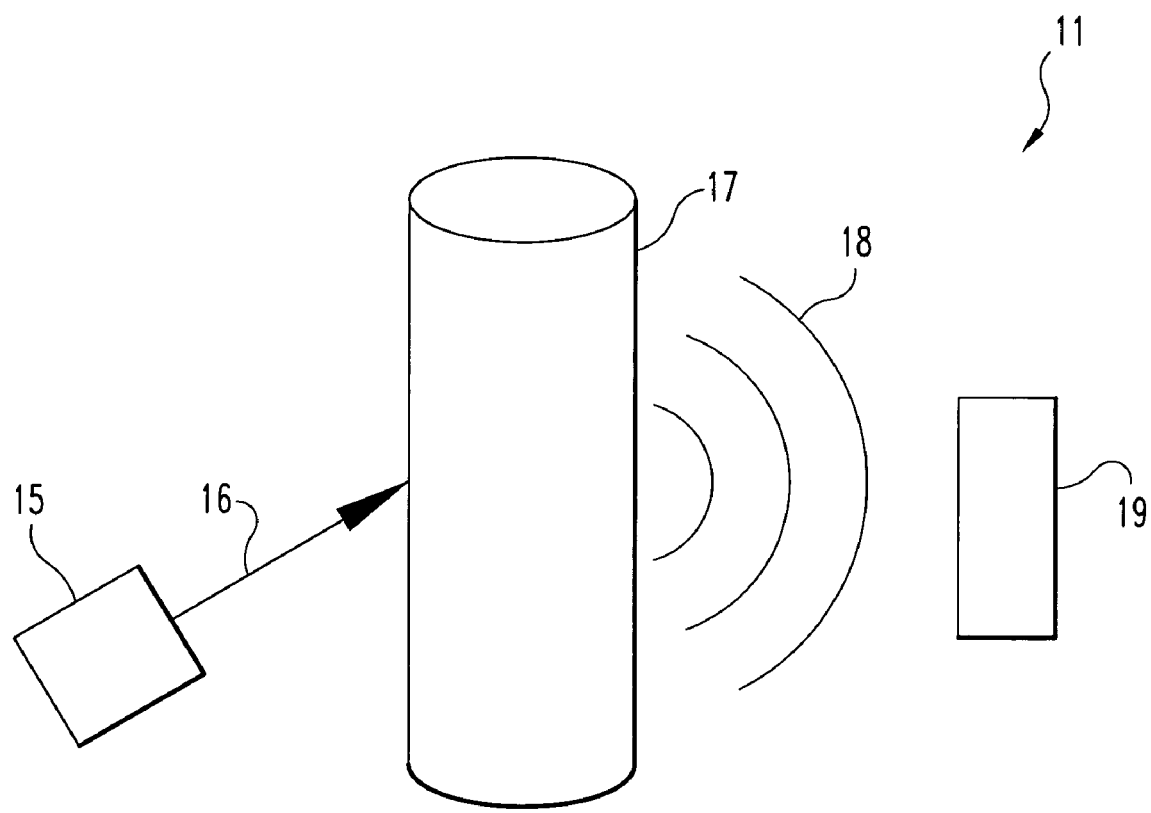
FIG. 3 is a schematic view of a flow through x-ray fluorescence spectrometer.

The presence of tagants in the lubricating fluid is the detected 66 over time using a suitable XRF device. A suitable in-line and on-board XRF is depicted in commonly owned U.S. Pat. No. 6,668,039. U.S. Pat. No. 5,982,847 to Nelson depicts another suitable flow-through x-ray fluorescence meter for on-board fluid analysis. The principal of operation of an XRF device is generally known and is described herein with reference to FIG. 3 which schematically illustrates a flow-through x-ray fluorescence meter 11. In the XRF meter 11, a sample fluid flows through conduit 17 and x-rays 16 from an x-ray source 15 interrogate the sample. When interrogated by the x-rays 16, atoms in the sample are excited, and as they relax from their excited energy levels they produce a fluorescence response 18. This response 18 is detected by a detector 19, which is typically a multi-channel detector. The detected response is then analyzed to determine the elemental content of the sample. A typical method of analysis is to quantitatively determine fluorescent photon counts for photons having different energy levels to determine a fluorescence spectrum. Then, knowing a priori the fluorescence spectrum for various atomic materials potentially in the sample, the detected fluorescence spectrum is mathematically resolved so as to determine the amounts of different atomic materials in the sample.

Having determined the amounts of the tagants in the lubricating fluid over time, the wear rates of the various tagant bearing components of the machine are then determined 68. These wear rates are calculated by calculating the changes in the detected levels of the tagants in the lubricating fluid on a tagant-by-tagant basis. The individual changes in each tagant level are then correlated with wear rates for each of the components based on the know initial concentration of each tagant in each of the wear surfaces. Preferably, the number of different tagants used in all of the parts together is equal to or greater than the number of tagant-bearing parts, for example with each individual part including at least one tagant not found in any other part. For example, in a simplified case, each wear surface contains a single, unique tagant uniformly dispersed in the wear surface. Accordingly, an increase in one tagant in the lubricating fluid directly corresponds to an increase in wear of a the corresponding component. Where a tagant is found in more than one part, a series of multi-variable equations may be constructed and mathematically solved where the change in concentration of each tagant in the lubricating fluid is modeled as a linear combination of the wear rates of each tagant-bearing part multiplied by the concentration of the respective tagant in the part. While embodiments are contemplated where each wear surface would include multiple tagants, it is to be understood that for individualized monitoring to be effective, each surface should have a signature tagant composition.

Figure 2:
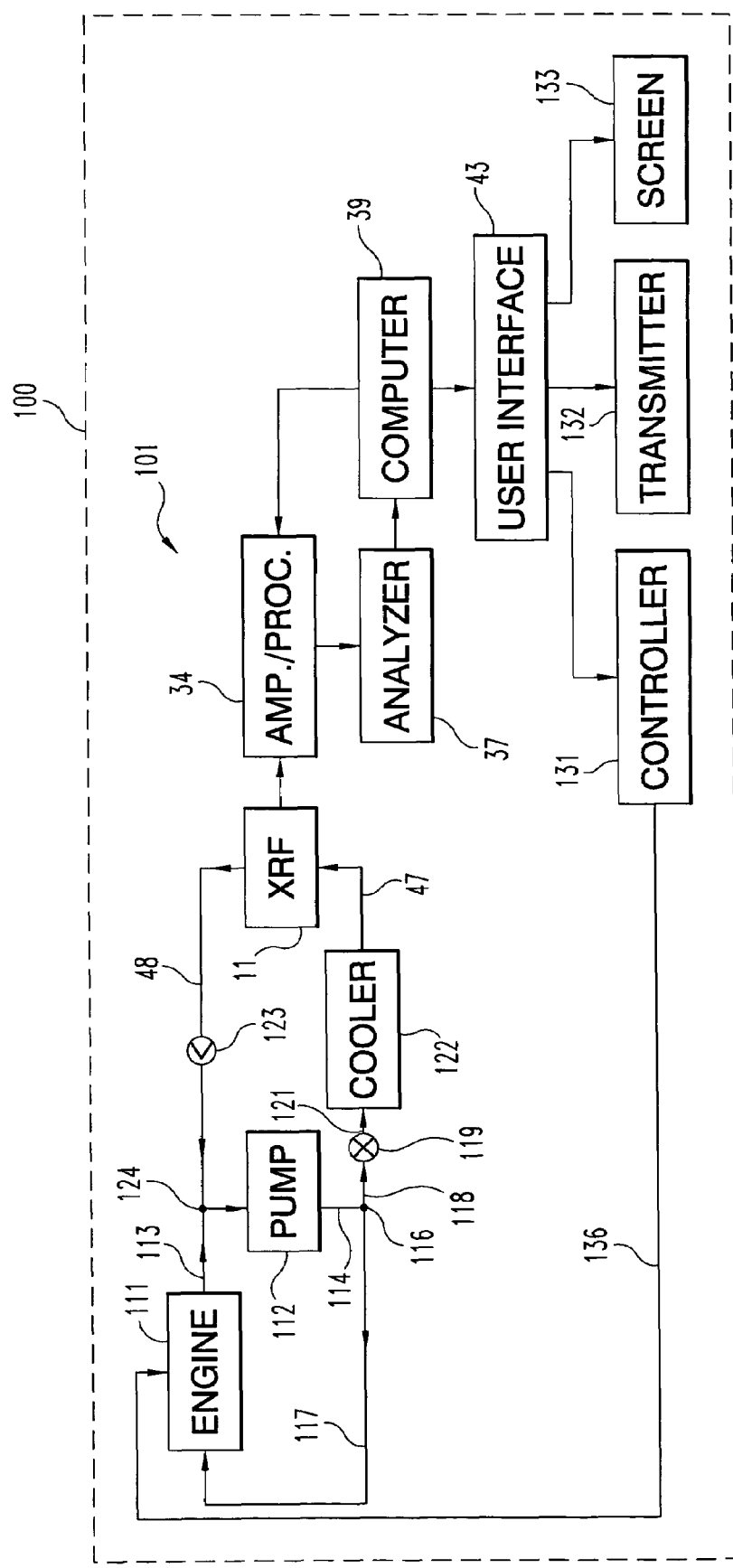
FIG. 2 is a block diagram of a system for determining the wear of engine components.

Turning now to FIG. 2, a system for machine health determination is schematically depicted. A machine, depicted as block 100, has on board, a system 101 for monitoring lubricating oil from an engine 111. The engine 111 has a lubricating oil pump 112 with a pump intake line 113 and discharge line 114. The discharge line has a tee junction at 116 to split the flow for supplying the engine on line 117 and supplying oil for sampling on line 118 to master valve 119. When valve 119 is open, a portion of the oil flowing in line 114 passes through valve 119, line 121 and oil cooler 122 into the oil sample line 47, which passes the oil through the x-ray fluorescence meter 11. Oil exiting the meter 11 on line 48 then passes through a one-way valve 123 before re-joining oil flow from the engine to the pump inlet at tee junction 124.

A signal processor 34 receives and amplifies the signals from the detector 19 of XRF meter 11 (see FIG. 3) under control of computer 39. Computer 39, receiving signals from the analyzer 37 and from any desired manual inputs, includes signal processing electronics and programming instructions operable to determine the presence and the amount of the tagants in line 47 based on the signals received from the detector 19.

The computer 39 can be any of many general purpose computers commercially available and programmed to cooperate with the analyzer 37 to perform the tasks normally related to x-ray fluorescence analysis according to the present invention. Alternatively, special purpose computers designed specifically to accomplish one or more of the tasks to implement the present invention can also be used. Tasks to be performed include collecting fluorescent x-ray intensity data, subtracting background data, and converting fluorescent x-ray data into concentration values for the tagants. Additional tasks to be performed by computer 39 include storing the tagant concentration data, determining changes in the tagant levels, and mathematically correlating those changes to wear and/or wear rates of specific parts.

Results determined by the computer are transmitted to a user interface 43 and then to a controller 131, for example, or to a viewing screen 133. These results can include a warning signal when the wear of one of the components exceeds a predetermined limit. An output signal line 136 is shown from controller 131 to the engine 111. The signal on such line could be used to control speed or load or to shut-down an engine in response to detection of a dangerous wear condition or impending failure of the engine due to excessive wear or destruction of one or more engine components. Other outputs from the computer 39 can be used to do any of a variety of things. For example a wireless transmitter 132 may be used to transmit the results to a remote observer or remote computer (not shown). This remote observe or computer (or the onboard computer) can collect the component-specific wear information and use it in scheduling maintenance and predicting failures of the machine.

In the illustrated embodiment, the flowing oil sampler is connected to oil line 116 separately from the main oil line 117, and thus interrogates oil selectively diverted from the main line. It is also contemplated that the sampler can be provided in oil line 114, 117 and thus be operable to interrogate all engine oil from pump 112 rather than a portion oil selectively diverted therefrom.

The machine components whose wear can be detected according to the present invention include bearings, shafts, journals, and any other wetted mechanical component. These components can be metallic or composite. A particular application of the present invention is in determining wear rates of different bearings in a turbine engine, for example a gas turbine engine or jet engine.

CLOSURE

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding. Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

What is claimed is:

1. A method for individually determining wear of various machine components comprising:
    providing a machine having a plurality of machine components, wherein each of the components has a wear surface of substantially identical material composition save that each wear surface has been doped with small amounts of at least one doping element, wherein the amounts of the doping elements in each of the wear surfaces is different; and
    determining the values corresponding to amounts of each doping element in a lubricating fluid of the machine by detecting a fluorescence response to x-ray interrogation of the lubricating fluid.

2. The method of claim 1 wherein the doping elements include at least one of vanadium, chromium, cobalt, gold, silver, tungsten, and indium.

3. The method of claim 1 wherein the wear surfaces are on components of a turbine.

4. The method of claim 1 wherein detecting the fluorescence response occurs on board the machine.

5. The method of claim 4 further comprising wirelessly transmitting signals representing the values to a remote observer of machine health.

6. A method comprising:
   monitoring wear of wear surfaces of machine parts by detecting an x-ray fluorescence response of a lubricating fluid to determine amounts of a plurality of tagants in the lubricating fluid,
   wherein each of wear surfaces contains one or more of the tagants and the tagant composition of each wear surface is different and,
   wherein tagants are initially present in an unworn state of at least one wear surface in a local concentration of between about 1 and 5 atomic percent.

7. A method for detecting wear of a family of components of a machine comprising:
   determining values corresponding to amounts of tagants in a lubricating fluid of a machine by detecting an x-ray fluorescence response of the lubricating fluid;
   wherein each member of the family of components has a signature composition of tagants in a wear surface, and
   wherein a wear surface of a first component includes at least two different tagants not found in the wear surface of a second component.

* * * * *